United States Patent
Terashima

(10) Patent No.: US 10,398,362 B2
(45) Date of Patent: Sep. 3, 2019

(54) MEASUREMENT DEVICE, MANAGEMENT DEVICE, MEASUREMENT SKILL MANAGEMENT SYSTEM, AND MEASUREMENT SKILL MANAGEMENT METHOD

(71) Applicant: PHC HOLDINGS CORPORATION, Tokyo (JP)

(72) Inventor: Noriyoshi Terashima, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 2 days.

(21) Appl. No.: 14/612,304

(22) Filed: Feb. 3, 2015

(65) Prior Publication Data
US 2015/0223741 A1 Aug. 13, 2015

Related U.S. Application Data

(60) Provisional application No. 61/937,579, filed on Feb. 9, 2014.

(51) Int. Cl.
*A61B 5/145* (2006.01)
*A61B 5/15* (2006.01)
(Continued)

(52) U.S. Cl.
CPC .... *A61B 5/14532* (2013.01); *A61B 5/150358* (2013.01); *G16H 10/40* (2018.01);
(Continued)

(58) Field of Classification Search
None
See application file for complete search history.

(56) References Cited

U.S. PATENT DOCUMENTS 4,421,122 A * 12/1983 Duffy .................. A61B 5/0484
600/544
6,157,808 A * 12/2000 Hollingsworth ......... G09B 7/02
434/219
(Continued)

FOREIGN PATENT DOCUMENTS

JP 2013-24880 A 2/2013
WO WO 9414129 A1 * 6/1994 ............. A61B 17/00
(Continued)

*Primary Examiner* — Eddy Saint-Vil
*Assistant Examiner* — William D Ermlick
(74) *Attorney, Agent, or Firm* — McDermott Will & Emery LLP

(57) ABSTRACT

A measurement device that measures a specific substance contained in a sample comprises a detector configured to detect a signal based on the specific substance contained in the sample, and a first controller configured to control an operation of the detector. The first controller executes a measurement operation that drives the detector to detect the signal based on the specific substance contained in the sample, and calculates concentration of the specific substance contained in the sample on the basis of the detected signal, and executes a test mode for the measurement operation. The first controller further executes a specific mode that prohibits execution of the measurement operation and only permits the measurement operation when the test mode is executed.

2 Claims, 7 Drawing Sheets

(51) Int. Cl.
  *G16H 10/40* (2018.01)
  *A61B 5/00* (2006.01)
  *A61B 90/90* (2016.01)

(52) U.S. Cl.
  CPC ......... *A61B 5/0004* (2013.01); *A61B 5/14546* (2013.01); *A61B 90/90* (2016.02); *A61B 2560/0475* (2013.01)

(56) References Cited

U.S. PATENT DOCUMENTS

| | | | | |
|---|---|---|---|---|
| 6,300,873 B1* | 10/2001 | Kucharczyk | ......... | A47G 29/141 235/382.5 |
| 7,532,942 B2* | 5/2009 | Reiner | ......... | G06F 19/321 700/90 |
| 8,495,707 B2 | 7/2013 | Miller | | |
| 8,797,180 B2 | 8/2014 | Weintraub et al. | | |
| 2003/0130567 A1* | 7/2003 | Mault | ......... | A61B 5/0022 600/300 |
| 2003/0233129 A1* | 12/2003 | Matos | ......... | A61B 5/0006 607/5 |
| 2004/0052679 A1* | 3/2004 | Root | ......... | A61B 1/00016 422/1 |
| 2004/0098582 A1* | 5/2004 | Mori | ......... | A63F 13/02 713/156 |
| 2007/0232885 A1* | 10/2007 | Cook | ......... | G06F 19/321 600/407 |
| 2008/0160488 A1* | 7/2008 | Younkes | ......... | G09B 7/04 434/219 |
| 2008/0294507 A1* | 11/2008 | Reiner | ......... | G06F 19/321 705/2 |
| 2010/0003657 A1* | 1/2010 | Shibui | ......... | G09B 23/30 434/267 |
| 2010/0050236 A1* | 2/2010 | Miller | ......... | G06F 19/3412 726/3 |
| 2013/0024247 A1 | 1/2013 | Ausdenmoore et al. | | |
| 2013/0184548 A1 | 7/2013 | Matsumura | | |
| 2013/0276521 A1 | 10/2013 | Fuerst et al. | | |
| 2013/0296719 A1* | 11/2013 | Packer | ......... | A61B 5/0205 600/484 |
| 2014/0159916 A1 | 6/2014 | Weintraub et al. | | |
| 2014/0315172 A1* | 10/2014 | Cheeks, Jr. | ......... | G09B 23/28 434/262 |
| 2014/0322683 A1* | 10/2014 | Baym | ......... | G06Q 50/22 434/219 |
| 2015/0029037 A1 | 1/2015 | Weintraub et al. | | |
| 2016/0300027 A1* | 10/2016 | Jensen | ......... | G01N 35/00623 |
| 2016/0321581 A1* | 11/2016 | Delgrande | ......... | G06Q 10/0633 |

FOREIGN PATENT DOCUMENTS

| | | | | |
|---|---|---|---|---|
| WO | WO 0117452 A1 * | 3/2001 | ............. | A61B 18/00 |
| WO | WO 2008034913 A2 * | 3/2008 | ......... | A61B 5/04842 |
| WO | 2011/141908 A2 | 11/2011 | | |
| WO | 2012/035725 A1 | 3/2012 | | |

\* cited by examiner

CURRENT DATE: 1/10/14

| OPERATOR IDENTIFICATION INFORMATION | REGISTRATION DATE | TEST TAKEN | TEST RESULT |
|---|---|---|---|
| OPERATOR a | 2014/1/4 | ✓ | ✓ |
| | 2013/7/9 | ✓ | ✓ |
| OPERATOR b | 2013/7/9 | ✓ | ✓ |
| | 2013/1/15 | ✓ | ✓ |
| OPERATOR c | 2014/1/4 | ✓ | NG |
| | 2013/7/9 | ✓ | ✓ |

FIG. 7 ated drawings and the following description so that a person skilled in the art might fully understand this disclosure, but do not intend for these to limit what is defined in the patent claims.

MEASUREMENT DEVICE, MANAGEMENT DEVICE, MEASUREMENT SKILL MANAGEMENT SYSTEM, AND MEASUREMENT SKILL MANAGEMENT METHOD

PRIORITY

This application claims priority based on U.S. provisional application 61/937,579 which was filed on Feb. 9, 2014.

BACKGROUND

Technical Field

The present application relates to a measurement device, to a management device, to a measurement skill management system in which a measurement device and a management device are used, and to a measurement skill management method in which a measurement device or a management device is used.

Background Art

Blood glucose level measurement devices used in hospitals, for example, are used when a nurse or the like (hereinafter referred to as an operator) measures the blood glucose level of a patient (see WO 2012/035725, for example). It is recommended that the operator undergo periodic testing or training in order to maintain or improve his or her skill at measuring blood glucose levels.

SUMMARY

The measurement device pertaining to one mode of the present application is a measurement device that measures a specific substance contained in a sample, the measurement device comprising a detector configured to perform a detection operation that detects a signal based on the specific substance contained in the sample, and a first controller configured to control an operation of the detector. The first controller drives the detector to detect the signal based on the specific substance contained in the sample, and executes a measurement operation that calculates concentration of the specific substance contained in the sample on the basis of the detected signal. The first controller executes a test mode for the measurement operation. The first controller executes a specific mode that prohibits execution of the measurement operation and only permits the measurement operation when the test mode is executed.

BRIEF DESCRIPTION OF DRAWINGS

FIG. 7 is a diagram of how a specific test is carried out with the management device pertaining to the embodiment.

DETAILED DESCRIPTION

Figure 1:
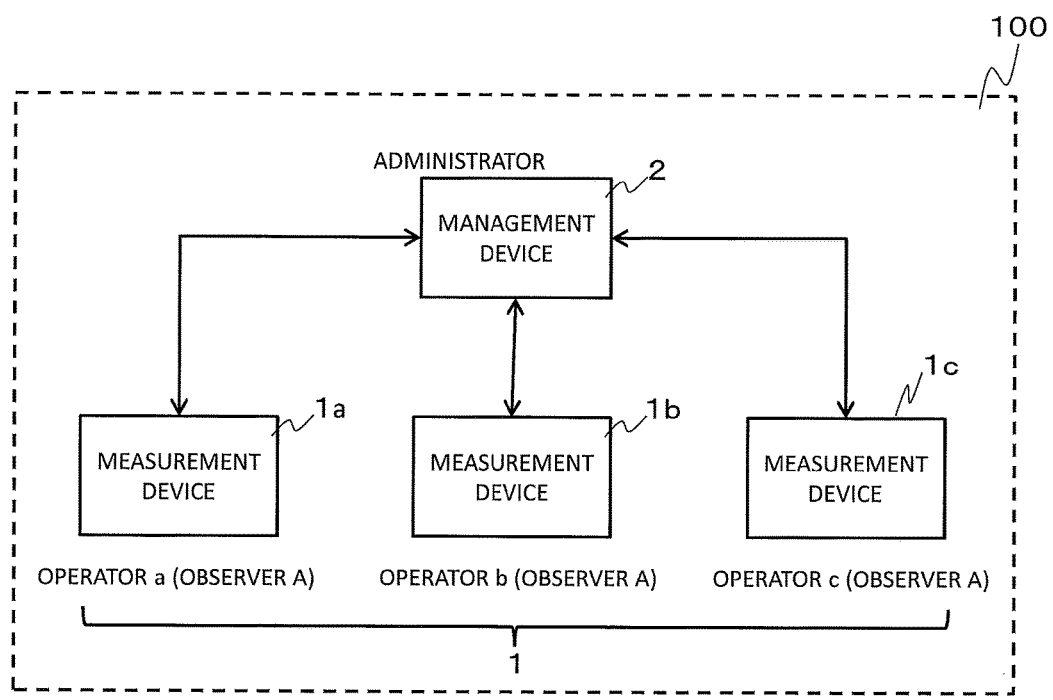
FIG. 1 is a simplified diagram of the configuration of a measurement skill management system pertaining to an embodiment.

Embodiments will now be described in detail through reference to the drawings as needed. However, some unnecessarily detailed description may be omitted. For example, detailed description of already known facts or redundant description of components that are substantially the same may be omitted. This is to avoid unnecessary repetition in the following description, and facilitate an understanding on the part of a person skilled in the art. The inventors have provided the appended drawings and the following description so that a person skilled in the art might fully understand this disclosure, but do not intend for these to limit what is defined in the patent claims.

Embodiments 1-1. Overview

The "operator" referred to in this embodiment is a person who uses a measurement device to measure a specific substance, and refers to someone who undergoes specific testing or training. A nurse is an example. The "observer" is a person who monitors the specific testing or training of the operator, and refers to someone who decides whether the test results of the operator are pass or fail. The "administrator" is a person who manages the implementation of the specific testing or training of the operator. The "user" is anybody who uses a measurement device, and mainly includes the operator and the observer.

The specific testing or training (hereinafter referred to simply as test) recommended for the operator will be described by using a blood glucose level measurement device used in a hospital as an example. The specific test recommended for the blood glucose level measurement device described below is one example.

The specific test recommended for the operator is a test for measuring the glucose concentration in a sample by using a blood glucose level measurement device. This test evaluates or confirms the measurement skill of the operator for using the blood glucose level measurement device, and is conducted under the supervision of the observer.

Tests include a quality control (QC) test and a patient test. The QC test and the patient test may both be administered to the operator as the specific test, or just one or the other may be administered. The QC test involves the use of a control liquid containing a known concentration of glucose as the sample, and is a test in which the operator uses a blood glucose level measurement device to measure the glucose concentration in the control liquid. The patient test involves the use of blood collected from a patient, and is a test in which the operator uses a blood glucose level measurement device to measure the glucose concentration in the patient's blood.

The administrator manages the implementation of the specific test by the operator (usually a number of people) using the blood glucose level measurement device. The administrator prompts the operator to take the specific test when the time for the operator to renew the specific test approaches (such as a month before the renewal deadline). For example, the operator is required to take the specific test every six months.

The operator then takes the specific test including at least one of the QC test and the patient test under the supervision of the observer. The observer decides whether or not the operator passes the test based on the test results, and records the renewal date and results for the specific test taken by the operator.

An operator who has passed the test is permitted by the observer to use a blood glucose level measurement device to measure a patient's blood glucose level until the next renewal deadline for the specific test. That is, an operator who did not pass the test, or an operator who did not take the specific test by the renewal deadline cannot use a blood glucose level measurement device to measure a patient's blood glucose level unless that operator passes the test. The observer and the administrator may also be the same person.

However, the administrator generally has to manage the implementation of a specific test for many operators in a hospital. Also, a hospital may have a plurality of measurement devices that require specific testing besides blood glucose level measurement devices. Consequently, the administrator has to manage the implementation of specific testing for many operators. Similarly, the observer must supervise the implementation of specific testing for many operators, and must manage how measurement devices are used by each operator based on the implementation of each specific test. As a result, the administrator and the observer carry a heavy management burden. Accordingly, there is the risk that the implementation of specific test for each operator, and the usage conditions for measurement devices may not be managed properly.

In view of this, the inventors conducted diligent study into a technique that would allow the implementation of specific operator testing or training that is carried out periodically to be managed more effectively, and arrived at the concept of the measurement device, management device, and measurement skill management system featuring a measurement device as an embodiment of the present application.

An embodiment of the present application will now be described through reference to the drawings. In this embodiment, a blood glucose level measurement device is described as an example, but the present application is not limited to or by this. Specifically, the measurement device and management device pertaining to an example of the present application can be applied to all measurement devices that require their operators to undergo periodic specific testing or training.

The measurement device, management device, and measurement skill management system pertaining to this embodiment will now be described through reference to the drawings.

1-2. Configuration
1-2-1. Configuration of Measurement Skill Management System

FIG. 1 is a simplified diagram of the configuration of the measurement skill management system pertaining to this embodiment. The measurement skill management system 100 shown in FIG. 1 comprises a plurality of measurement devices 1 (an example of a measurement device) and a management device 2 (an example of a management device) that can be connected to each of the measurement devices 1. The measurement skill management system 100 pertaining to this embodiment has three measurement devices 1a to 1c, for example, but the present application is not limited to or by this, and there may be one or more of the measurement devices 1. Also, the measurement devices 1a to 1c shown in FIG. 1 are capable of administering a test to the same subject. That is, the operator may use any of the measurement devices 1a to 1c to take the same specific test. The measurement skill management system 100 pertaining to an embodiment of the present application may manage the measurement devices 1 with the management device 2 in a single hospital, or may manage the measurement devices 1 in a plurality of hospitals with a single management device 2. Alternatively, the measurement devices 1 in a specific department of a single hospital may be managed by the management device 2.

1-2-2. Configuration of Measurement Devices

The measurement device 1 measure a specific substance contained in a liquid sample collected from a patient (such as blood, urine, or saliva).

Figure 2:
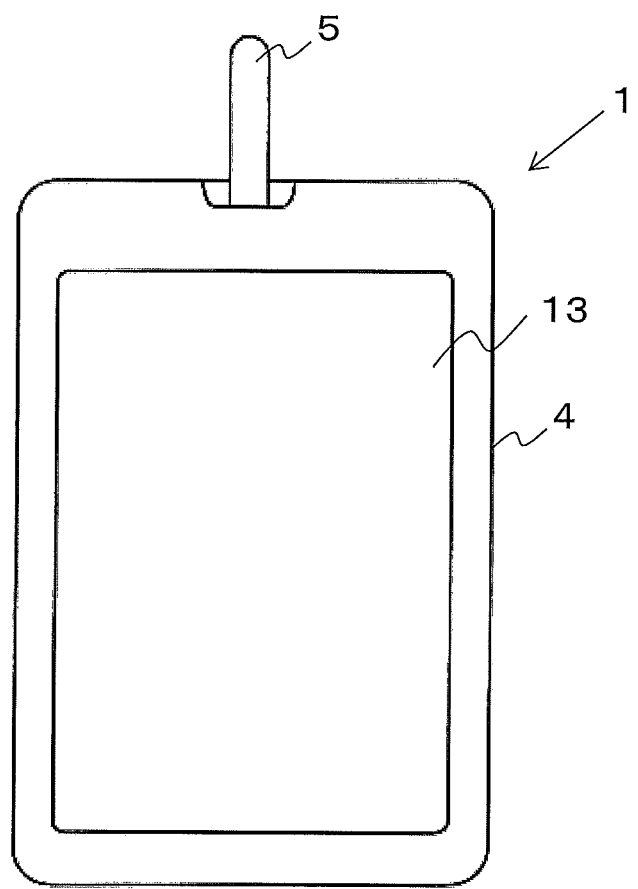
FIG. 2 is a diagram of an example of the appearance of a measurement device (blood glucose level measurement device) pertaining to the embodiment.

FIG. 2 is a diagram of an example of the appearance of the measurement device 1 pertaining to this embodiment. The measurement device 1 shown in FIG. 2 is, for example, a blood glucose level measurement device for hospital use. The measurement device 1 includes a main body 4 and a sensor 5. The main body 4 is configured to allow the sensor 5 to be removably attached. The operator can measure the glucose concentration in the patient's blood by mounting the sensor 5 to the main body 4 and in this state depositing a drop of the blood (taken from a fingertip, for example) on the sensor 5.

Figure 3:
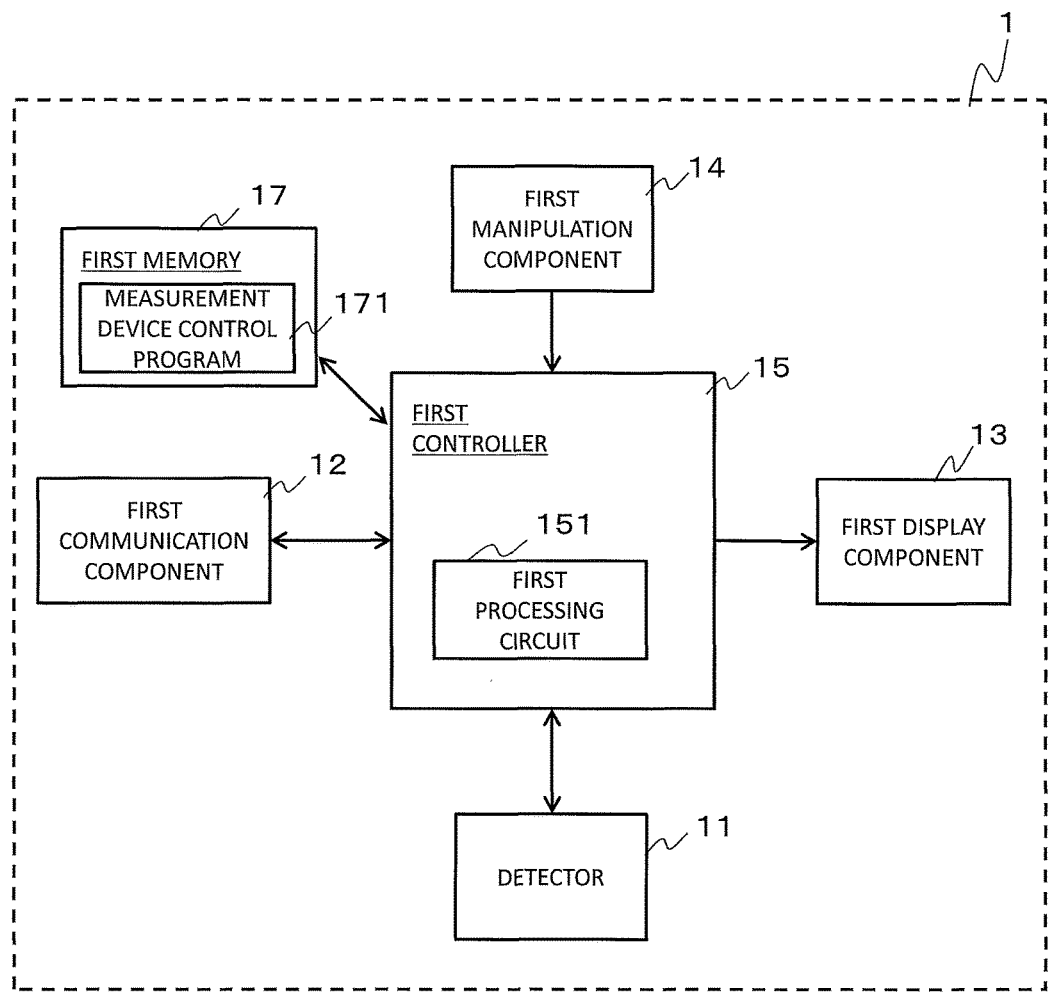
FIG. 3 is a simplified diagram of the configuration of the measurement device pertaining to the embodiment.

FIG. 3 shows an example of the internal configuration of the measurement device 1 pertaining to this embodiment. The measurement device 1 comprises a detector 11 (an example of a detector), a first communication component 12 (an example of a first communication component), a first display component 13, a first manipulation component 14 (an example of a first manipulation component), a first controller 15 (an example of a first controller), and a first memory 17 (an example of a first memory).

<Detector>

The detector 11 detects a signal based on a specific substance contained in a sample. This signal based on a specific substance can be, for example, an electrochemical signal (such as electrical current), absorbency, turbidity, fluorescence, emission (chemical emission, biological emission, electrochemical emission, etc.), or the like. The detector 11 is equipped with a detecting mechanism that corresponds to a detection signal.

If the measurement device 1 is a blood glucose level measurement device, the signal based on a specific substance is an electrochemical signal, for example. In this case, the detector 11 has a connector that includes an electrode, and when the sensor 5 (FIG. 2) is mounted to the main body 4 of the blood glucose level measurement device, the sensor 5 is connected to the electrode of the connector of the detector 11.

The sensor 5 mainly comprises a substrate on which an electrode pattern is formed, and a reagent disposed on the substrate. The reagent includes a redox enzyme (glucose oxidase or glucose dehydrogenase). The use of an electronic mediator is an example of a method for electrochemical detection. In this case, the reagent includes an electronic mediator that is potassium ferricyanide or a quinone compound. For example, when blood is deposited on the sensor 5, mainly the glucose in the blood, redox enzyme, and electronic mediator react, and the measurement device 1 applies a specific voltage to detect the current, of which magnitude changes depending on the glucose concentration. With the magnitude of this current, the glucose concentration in the blood can be measured.

<First Communication Component>

The first communication component 12 includes a communication interface for connecting the measurement device 1 to the management device 2. The first communication component 12 may use wired communication or wireless communication. Alternatively, it may comprise both wired and wireless interfaces.

<First Display Component>

The first display component 13 is used to give various displays, and is a liquid crystal display, for example. In the example in FIG. 1, the first display component 13 includes a touch panel having a sensor for detecting touch, and is also combined with the function of the first manipulation component 14. Specifically, the user can perform various operations on the measurement device 1 by touching soft keys displayed by the first display component 13. However, the first display component 13 is not limited to a touch panel type, and may instead comprise separate hard keys as the first manipulation component 14. Or, it may comprise both a touch panel and hard keys.

<First Manipulation Component>

The first manipulation component 14 is used by the user for various input operations. The input information that is inputted via the first manipulation component 14 is outputted to the first controller 15.

Although not shown in the drawings, the first manipulation component 14 may be configured to include a code reader. The code reader reads an information code from a tag attached to the subject. This tag includes information codes, such as a one-dimensional bar code, a two-dimensional QR code, a magnetic tag, or an RF tag (IC tag), and specific information is recorded in these information codes. A code reader reads an information code that includes unique information (such as strip lot verification) on a tag attached to the sensor 5, or to a container, package, or the like that holds the sensor 5. For example, the code reader reads an information code that includes unique information on a tag attached to a bottle of a control liquid used to perform a QC test. The code reader may also read, for example, an information code that includes unique information such as patient identification information (such as a patient ID) that will be a subject for which the measurement device 1 measures. The code reader may also read, for example, an information code that includes unique information such as identification information for the operator using the measurement device 1 (such as an operator ID). The code reader may also read, for example, an information code that includes unique information such as identification information for the operator's supervisor (such as a supervisor ID). A code reader is just an example, and the configuration may be such that information read by the above-mentioned code reader is instead directly inputted with soft or hard keys. Also, the input to the first manipulation component 14 in the present application is not limited to input via soft or hard keys, and the reading of an information code via a code reader is also encompassed.

<First Controller 15>

The first controller 15 controls the blocks in the measurement device 1, and performs various kinds of computation, information processing, and so forth. The first controller 15 is, for example, a microprocessor that includes a CPU or a processor. The first controller 15 includes a first processing circuit 151.

The first processing circuit 151 suitably reads and executes a measurement device control program 171 stored in a first memory 17.

<First Memory 17>

The first memory 17 is a semiconductor memory, a magnetic recording medium, an optical recording medium, or the like. Various kinds of information are stored in the first memory 17, and this various information includes the measurement device control program 171. The measurement device control program 171 may be such that it is temporarily read into the first memory 17.

The first memory 17 is configured to store identification information about a user. The user identification information stored in the first memory 17 can be successively added, deleted, or modified. The user identification information stored in the first memory 17 includes identification information about the operator and identification information about the observer. The first memory 17 stores the operator identification information in a first segment, and the observer identification information in a second segment. The first memory 17 can also store the user identification information overlapping the first segment and second segment.

<Measurement Device Control Program>

The measurement device control program 171 includes the following first to eighth measurement programs.

(i) First Measurement Program

The first measurement program drives the detector 11 under the control of the first processing circuit 151, and causes it to detect a signal based on a specific substance contained in a sample. The first measurement program then causes the first processing circuit 151 to calculate the concentration of the specific substance contained in the sample on the basis of a signal based on the specific substance.

With the hospital-use blood glucose level measurement device 1, for example, the operator mounts the sensor 5 to the main body 4 to electrically connect the sensor 5 to the main body 4, which completes the preparation for measuring the concentration of the specific substance contained in the sample. The sample is then deposited on the sensor 5, whereupon the reagent in the sensor 5 reacts with the glucose contained in the sample, a specific voltage is applied, for example, and an electrochemical signal that changes depending on the glucose concentration is detected. The first processing circuit 151 uses a table or a formula stored in the first memory 17 for calculating the glucose concentration, and calculates the glucose concentration from the detected electrochemical signal. The table or formula for calculating the glucose concentration may be different for each manufacturing lot of the sensor 5.

The first processing circuit 151 may output the measured value for glucose concentration to the first display component 13. This allows the operator to ascertain the glucose concentration by checking the first display component 13.

(ii) Second Measurement Program

The second measurement program actuates the first measurement program in a specific test mode. The test mode in the second measurement program is a mode of conducting a quality control test and/or a mode of conducting a patient test.

Figure 4:
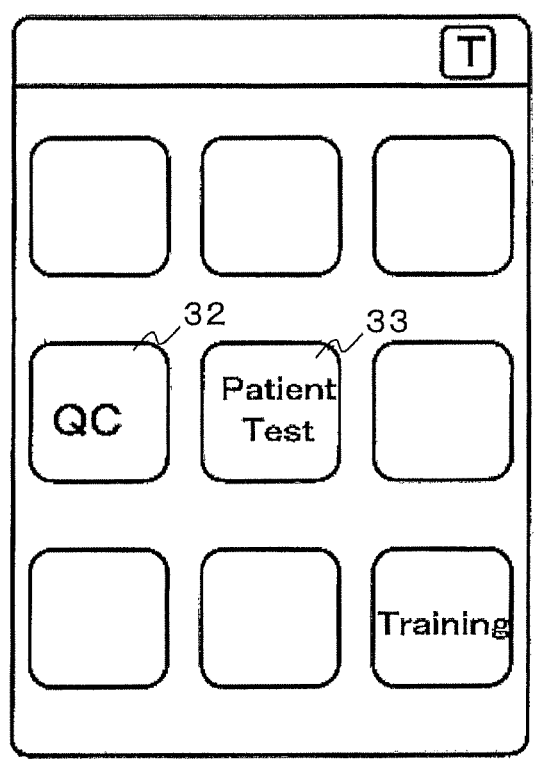
FIG. 4 is a diagram of an example of the screen displayed on a first display component of the measurement device pertaining to the embodiment.

The operator actuates the second measurement program by using the first manipulation component 14 to make a specific input. As shown in FIG. 4, for example, an icon 32 for selecting a QC test and an icon 33 for selecting a patient test are displayed on the first display component 13 for selecting the test mode. The operator selects one of the icons to actuate the QC test mode or the patient test mode as the test mode, and to execute the first measurement program in the selected test mode.

(iii) Third Measurement Program

The third measurement program executes the following processing (an example of a specific mode). The third measurement program puts the first processing circuit 151 in a state in which execution of the first measurement program is prohibited. When the third measurement program is executed, the first measurement program cannot be executed. Specifically, the measurement device 1 can no longer be used to measure the specific substance. However, in a state in which a specific test mode (QC test mode or patient test mode) is actuated by the second measurement program, the third measurement program terminates the state in which execution of the first measurement program by the first processing circuit 151 is prohibited.

To execute the third measurement program, the input information inputted with the first manipulation component 14 is compared to identification information for a second user (observer) stored in the second segment of the first memory 17, and the program cannot be executed if the input information is confirmed to be identification information for the second user (observer). When the user logs in as an observer, the program is executed according to the specific input made with the first manipulation component 14. That is, the third measurement program cannot be executed if the user cannot log in to the measurement device 1 as an observer.

Also, the third measurement program may halt the execution of the first measurement program of the measurement device 1, but may be able to allow the execution only for the identification information for a particular user out of the identification information for plural first users (operators) stored in the first segment of the first memory 17. With this configuration, the measurement operation can be executed if one operator has logged in to the measurement device 1, but the measurement operation cannot be executed for another operator even though that operator has logged in to the measurement device 1.

The third measurement program is executed, for example when the first manipulation component 14 is used to make a specific input. In this case, it is preferable that only someone other than the operator (the observer) is allowed to execute the third measurement program. For instance, if just the observer is allowed to execute the third measurement program, the first processing circuit 151 confirms the match between the input information inputted with the first manipulation component 14 and the identification information for a plurality of users stored ahead of time in the first memory 17 (determines whether the two match). Here, the third measurement program is executed if a specific input is made to the first manipulation component 14. That is, the third measurement program can be actuated only if a person has logged in as an observer. The measurement device 1 allows the user to choose to log in as an observer or an operator via the first manipulation component 14. If the user has chosen to log in as an observer, the device performs comparison and matching among the identification information of users assigned to the second group.

The third measurement program may, for example, be executed according to a specific command from the management device 2 received via the first communication component 12. The third measurement program is executed for the identification information of a particular user assigned to the first group of the first memory 17, according to the specific command from the management device 2.

The third measurement program is executed in one or more of the following first to fourth modes. In the first mode, the third measurement program is executed according to a specific input via the first manipulation component 14 of the measurement device 1. When the third measurement program is thus executed, the execution of the third measurement program is terminated by a fourth measurement program (discussed below) that is executed according to a specific input made with the first manipulation component 14. In the second mode, the third measurement program is executed according to a specific command from the external management device 2 received via the first communication component 12. When the third measurement program is thus executed, the execution of the third measurement program is terminated by a fifth measurement program (discussed below) that is executed according to a specific command from the external management device 2. In the third mode, the third measurement program is executed according to a specific input through the first manipulation component 14 of the measurement device 1. When the third measurement program is thus executed, the execution of the third measurement program is terminated by the fifth measurement program (discussed below) that is executed according to a specific command from the external management device 2. In the fourth mode, the third measurement program is executed according to a specific command from the external management device 2 received via the first communication component 12. When the third measurement program is thus executed, the execution of the third measurement program is terminated by the fourth measurement program (discussed below) that is executed according to a specific input made with the first manipulation component 14.

(iv) Fourth Measurement Program

The fourth measurement program halts the execution of the third measurement program according to a specific input made with the first manipulation component 14 to the first processing circuit 151. That is, when the fourth measurement program is executed, the execution of the third measurement program is terminated, and the specific substance can be measured with the measurement device 1.

(v) Fifth Measurement Program

The fifth measurement program halts the execution of the third measurement program according to a specific command from the management device 2 received via the first communication component 12. That is, when the fifth measurement program is executed, just as in the fourth measurement program, the execution of the third measurement program is terminated, and the specific substance can be measured with the measurement device 1.

(vi) Sixth Measurement Program

The sixth measurement program is a so-called login function for an operator. If a person cannot log in under the sixth measurement program, neither the specific test nor the measurement of the specific substance with the measurement device 1 can be performed.

The sixth measurement program compares input information that was inputted to the first processing circuit 151 via the first manipulation component 14, with identification information for a plurality of users (operators) stored ahead of time in the first segment of the first memory 17. If the input information matches (is validated to be) identification information for the plurality of users (operators) stored in the first segment of the first memory 17 (that is, if the person has logged in as an operator), then the first processing circuit 151 puts the first measurement program in an executable state.

(vii) Seventh Measurement Program

The seventh measurement program is a function for allowing only an observer to evaluate the results of the specific test taken by an operator.

The seventh measurement program performs control so that only a user who has logged in as an observer is allowed to input the evaluation result for result of the first measurement program executed in the test mode by an operator, to the first processing circuit 151 via the first manipulation component 14. The seventh measurement program then stores in the first memory 17 the evaluation result inputted by the user logged in as an observer.

(viii) Eighth Measurement Program

The eighth measurement program allows the first processing circuit 151 to send the evaluation result stored in the first memory 17 by the seventh measurement program to the management device 2 via the first communication component 12, along with identification information for first users (operators).

In particular, with the seventh and eighth measurement programs, the evaluation result can be inputted with the first manipulation component 14 with respect to the result of a test mode executed by the second measurement program for the operator stored in the first memory 17. This evaluation result cannot be inputted unless the person has logged in as a second user (that is, an observer) with his or her identification information stored in the second segment of the first memory 17. With this configuration, the observer can input the evaluation of the test result (pass or fail) for the specific test taken by the operator. Also, this evaluation result can be sent through the first communication component 12 to the external management device 2 along with identification information for the user who underwent the test mode.

1-2-3. Configuration of Management Device

The management device 2 provides a data management system (DMS), and is a computer that manages the measurement device 1 and the implementation of the specific test for operators.

Figure 5:
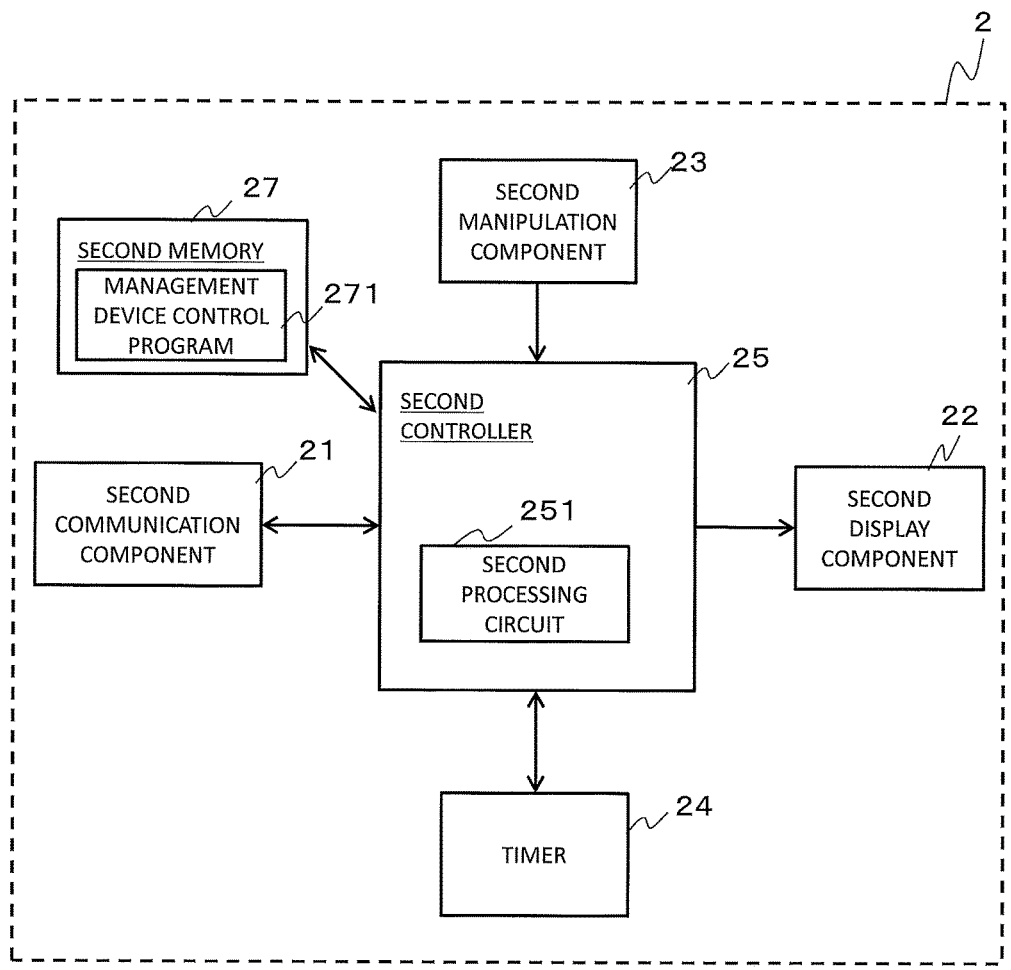
FIG. 5 is a simplified diagram of the configuration of a management device pertaining to the embodiment.

FIG. 5 shows an example of the internal configuration of the management device 2 pertaining to this embodiment. The management device 2 comprises a second communication component 21 (an example of a second communication component or a communication component), a second display component 22, a second manipulation component 23, a timer 24 (an example of a timer), a second controller 25 (an example of a second controller or a controller), and a second memory 27 (an example of a second memory or a memory). The management device 2 may be the result of introducing a dedicated program into a personal computer, or may be a dedicated terminal.

<Second Communication Component>

The second communication component 21 includes a communication interface for connecting the measurement device 1 and the management device 2. The second communication component 21 may use wired communication or wireless communication. Alternatively, it may comprise both wired and wireless interfaces. The second communication component 21 is a communication means capable of communicating with the first communication component 12 of the measurement device 1.

<Second Display Component>

The second display component 22 is used to perform various kinds of display, and is a liquid crystal display, for example. The second display component 22 includes a touch panel having a sensor for detecting touch, and is also combined with the function of the second manipulation component 23. However, the second display component 22 is not limited to a touch panel type, and may instead comprise separate hard keys as the second manipulation component 23. Or, it may comprise both a touch panel and hard keys.

<Second Manipulation Component>

The second manipulation component 23 is used by the user for various input operations. The input information that is inputted via the second manipulation component 23 is outputted to the second controller 25.

<Timer>

The timer 24 is what is called a clock. The timer 24 outputs the current time according to a command from the second controller 25.

<Second Controller>

The second controller 25 is used to control the blocks in the measurement device 1, and performs various kinds of computation, information processing, and so forth. The second controller 25 is, for example, a microprocessor that includes a CPU or a processor. The second controller 25 includes a second processing circuit 251.

The second processing circuit 251 suitably reads and executes a management device control program 271 stored in the second memory 27.

<Second Memory 27>

The second memory 27 is a semiconductor memory, a magnetic recording medium, an optical recording medium, or the like. Various kinds of information are stored in the second memory 27, and this various information includes the management device control program 271. The management device control program 271 may be such that it is temporarily read into the second memory 27.

The second memory 27 is configured to be able to store identification information about users (operators and observers), the implementation dates and results of past specific tests taken by operators, and identification information about a plurality of measurement devices 1 connected to the management device 2. This information can be successively added, deleted, or modified. The second memory 27 stores the operator identification information in a first segment, and the observer identification information in a second segment. The second memory 27 can also store the user identification information overlapping the first segment and second segment. The second memory 27 may be a recording medium provided within the management device 2, or may be a server connected wirelessly or by wire to the management device 2, and may have both configuration.

<Management Device Control Program>

The management device control program 271 includes the following first to fourth management programs.

(i) First Management Program

When the first management program is executed, the second communication component 21 receives first information sent from the measurement device 1 that executes the eighth measurement program. The first information includes verification information and implementation information of the test (information on whether or not the test was administered, the test evaluation result, etc.) for a first user (operator). The second processing circuit 251 stores the received first information, which is associated with identification information for a first user (operator) stored in the second memory 27. The second processing circuit 251 then outputs the current time from the timer 24, and also stores the outputted current time along with the first information. As a result of executing the first management program, the implementation information of the specific test can be acquired and managed for user identification information stored in the second memory 27 of the management device 2.

(ii) Second Management Program

The second management program causes the second processing circuit 251 to extract the newest first information from among the one or more sets of first information for a user stored in the second memory 27, and determines whether or not the current time outputted from the timer 24 is within a specific time period since the time when this newest first information was recorded. The management device 2 executes the second management program periodically, such as once a month. For example, if the renewal period for the specific test is six months, the second management program determines whether or not the current time is within six months since the time when the newest first information was recorded.

The second management program then extracts first information that is determined to have passed the specific test by the measurement device 1 executing the seventh measurement program. That is, only first information that has passed the QC test and the patient test (one or both) is extracted.

(iii) Third Management Program

The third management program sends a command through the second communication component 21 to the measurement device 1 to execute the third measurement program when the second processing circuit 251 has determined that the recorded date of the newest first information extracted by execution of the second management program is not within a specific time period. The second processing circuit 251 then gives a command to execute the third measurement program on the subject user identification information.

(iv) Fourth Management Program

The fourth management program sends a command through the second communication component 21 to the measurement device 1 to halt the execution of the third measurement program when the second processing circuit 251 has executed the first management program after the above-mentioned specific time period has elapsed. For example, if the renewal period for the specific test is six months, the measurement operation of the measurement device 1 is limited by the third measurement program in the measurement device 1 via the third management program when the specific test is not passed or is not taken after the six month period has elapsed. However, if the specific test has been taken and passed after the six month period has elapsed, then at the point when the test result or the like is recorded in the management device 2 by the first management program, the fourth management program sends the measurement device 1 a command to halt the execution of the third measurement program in the measurement device 1. Upon receiving this command, the measurement device 1 executes the fifth measurement program and the measurement device 1 is put into a state in which the measurement operation can be executed.

1-3. Operation of Measurement Device 1 and Management Device 2

Figure 6:
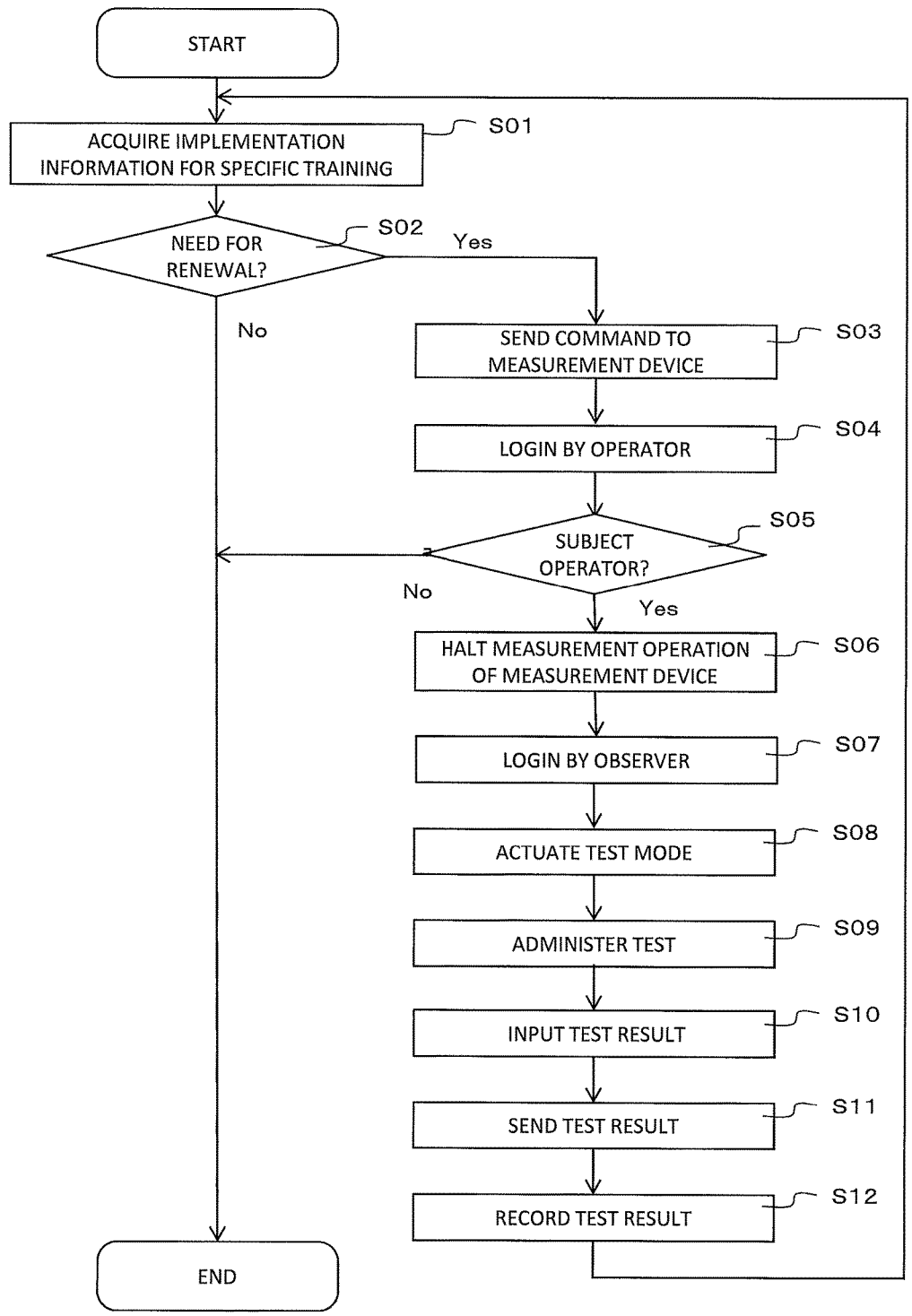
FIG. 6 is a flowchart of an example of the operation of the measurement skill management system pertaining to the embodiment.

An example of the operation of the measurement device 1 and the management device 2 configured as above will be described through reference to the flowchart in FIG. 6. The operation flowchart in FIG. 6 shows the operation of the measurement device 1 and the management device 2, or the operation of the measurement skill management system 100.

In the operation flowchart discussed below, we will assume that the renewal period for the specific test for the operator is six months, the current date is Jan. 10, 2014, and the specific test is to be implemented within one month prior to the renewal due deadline. The implementation period for the specific test (such as within one month prior to the renewal deadline) may be conveyed to the operator and observer by a reminder function from the management device 2, or the administrator may use the management device 2 or another notification means to notify the operator and observer. To simplify the description, the operators a to c will be described as all having the same specific test renewal deadline (Jan. 9, 2014), but in actual practice operators will usually have different renewal deadlines.

<Step S01>

In step S01, the second controller 25 of the management device 2 executes a management device control program, and extract the newest first information from the one or more sets of first information for the user (operator) stored in the second memory 27. The management device 2 then determines whether or not the time outputted from the timer 24 is within a specific length of time since the time when the newest first information was recorded.

As shown in FIG. 7, for example, operator identification information for operators a to c, and first information corresponding to the operators are stored in the second memory 27 of the management device 2. Here, the first information is stored as including the implementation date of the specific test for each operator (the time when the first information is recorded), and information on the test implementation (whether or not the test was taken, and whether the test was pass or fail). The test implementation date may include only the date when the previous first information was recorded, or as shown in FIG. 7, may include all or part of the past recorded dates.

The second processing circuit 251 extracts the newest first information for each operator in the second memory 27. For example, the recorded date of the newest first information is Jan. 4, 2014 for operator a, Jul. 9, 2013 for operator b, and Jan. 4, 2014 for operator c. The second processing circuit 251 extracts this newest first information.

The second processing circuit 251 of the management device 2 then checks on the pass/fail test result for the extracted newest first information. In the example in FIG. 7, operator a passed the test implemented on Jan. 4, 2014, operator b passed the test implemented on Jul. 9, 2013, and operator c did not pass the test implemented on Jan. 4, 2014.

<Step S02>

In step S02, the second processing circuit 251 of the management device 2 determines whether or not the specific test has been renewed, from the newest first information extracted for each operator. The determination categories are the recorded date for the newest first information, and the test result.

If we assume that today is Jan. 10, 2014, since the recorded date for the newest first information for operator a is Jan. 4, 2014, the renewal deadline for the next specific test is Jul. 3, 2014, and the test result is a pass. Therefore, the management device 2 at this checking determines that there is no need for renewal of the specific test by operator a (choosing "No" in S02 in FIG. 6), and this flow is ended.

The recorded date for the newest first information for operator b is Jul. 9, 2013, so the renewal deadline for the next specific test is Jan. 9, 2014. Since today is Jan. 10, 2014, the renewal deadline has already passed. Therefore, the management device 2 determines the operator b needs to renew the specific test (choosing "Yes" in S02 in FIG. 6), and the process moves to step S03.

The recorded date for the newest first information for operator c is Jan. 4, 2014, so the renewal deadline for the next specific test is Jul. 3, 2014, but the test result is a fail. Thus, the renewal deadline for the next specific test remains at Jan. 9, 2014. Since today is Jan. 10, 2014, the renewal deadline has passed and the test result is not a pass. Therefore, the management device 2 determines that operator c needs to renew the specific test (choosing "Yes" in S02 in FIG. 6), and the process moves to step S03.

<Step S03>

In step S03, the second processing circuit 251 of the management device 2 issues a command to execute the third measurement program to the measurement device 1 via the second communication component 21, by running the third management program. This time, operators b and c are subject to the execution of the third measurement program.

The second processing circuit 251 of the management device 2 may issue a command to all of the measurement devices 1a to 1c in FIG. 1, or may issue a command to just the measurement devices 1b and 1c. This can be set as desired according to how the measurement devices are used in the hospital. Specifically, if a measurement device 1 is provided to each operator for exclusive use in a hospital, then it suffices to issue a command to the measurement devices 1b and 1c that are used by the operators b and c respectively. However, the measurement device 1 may not always be used by the same operator in a hospital, or two or more operators may use a single measurement device 1. In this case, a command must be issued to all of the measurement devices 1 within the measurement skill management system 100. The description here will be of an example of the latter case.

The transmission of commands by the management device 2 in this step S03 may be performed as needed after the measurement device 1 is actuated and connected to the management device 2. The measurement device 1 stores the commands received from the management device 2 in the first memory 17.

<Step S04>

In step S04, the operator c logs in to the measurement device 1 using his own identification information. We will assume here that the measurement device 1 and the management device 2 have already been connected.

In this process, the sixth measurement program is executed by the first processing circuit 151 of the measurement device 1. The operator c, for example, inputs information via the first manipulation component 14 to log in. The login to the measurement device 1 may be executed by direct input using hard or soft keys, or by having a code reader read an information code assigned to operator c.

Here, of operators b and c, we will assume that operator c has logged in.

<Step S05>

The first processing circuit 151 of the measurement device 1 determines whether or not the logged-in operator is the operator who is to be subjected to the third measurement program. This determination is performed by the first processing circuit 151 of the measurement device 1 on the basis of a command from the management device 2 stored in the first memory 17.

Since the subject is operator c, the process moves to step S06. If an operator who is not supposed to take the test logs in (such as operator a), the third measurement program will not be applicable, so the third measurement program is not executed. Specifically, the measurement device 1 allows operator a to perform the normal measurement operation since the first measurement program is in an executable state.

The operator login (verification processing) in steps S04 and S05 need not be executed in a usage mode in which a dedicated measurement device 1 is assigned to each operator and identification information for a single operator is registered in each measurement device 1.

<Step S06>

The first processing circuit 151 of the measurement device 1 actuates the third measurement program. At this point the first processing circuit 151 performs control to prohibit the execution of the first measurement program (that is, the execution of the measurement operation) by using the identification information for operator c. Consequently, operator c cannot execute a measurement operation with the measurement device 1 in the measurement skill management system 100 by using his own identification information.

<Step S07>

In step S07, observer A logs in to the measurement device 1 using his own identification information. For example, observer A logs in by inputting the identification information through the first manipulation component 14. Login to the measurement device 1 may be executed by direct input using hard or soft keys, or by using a code reader to read an information code assigned to observer A.

<Step S08>

In step S08, the second measurement program of the measurement device 1 is actuated by manipulation from operator c. Although the first measurement program cannot be executed using the identification information for operator c, if the second measurement program for executing the test mode is actuated under execution of the third measurement program for which the observer has been verified, then execution of the first program, that is, a measurement operation, will be possible.

Operator c actuates the second measurement program by touching the icon 32 for QC test mode or the icon 33 for patient test mode on the screen of the first display component 13 shown in FIG. 4, for example.

<Step S09>

In step S09, operator c executes a QC test or a patient test. That is, the first measurement program is executed in a state in which the second measurement program is being actuated.

For example, operator c mounts the sensor 5 to the main body 4, and deposits a control liquid on the sensor 5 if it is a QC test, or deposits the patient's blood on the sensor 5 if it is a patient test. The measurement device 1 then executes measurement of a specific substance in the deposited sample, and the measurement result is displayed on the first display component 13, for example. Step S09 is carried out under the supervision of observer A.

<Step S10>

In step S10, observer A evaluates the test result for operator c by means of the seventh measurement program. Observer A inputs the test result for operator c.

<Step S11>

In step S11, under the execution of the eighth measurement program, the measurement device 1 sends at least the test result and the identification information for operator c as first information to the management device 2 via the first communication component 12.

Step S11 may be executed along with the input in step S10, or may be executed through separate manipulation of the first manipulation component 14 by observer A.

After this, the process returns to step S01, and the same steps are repeated.

Steps S05 to S12 are executed in the same way when operator b logs in.

1-4. Effect, etc.

The measurement device 1 pertaining to an embodiment of the present application (an example of a measurement device) measures a specific substance contained in a sample, and comprises the detector 11 (an example of a detector) configured to detect a signal based on the specific substance contained in the sample, and the first controller 15 (an example of a first controller) configured to control an operation of the detector 11. The first controller 15 drives the detector 11 to detect the signal based on the specific substance contained in the sample, and executes a measurement operation that calculates the concentration of the specific substance contained in the sample on the basis of the detected signal, and executes a test mode for the measurement operation. The first controller 15 also executes a specific mode that prohibits execution of the measurement operation and only permit the measurement operation when the test mode is executed.

With this configuration, for example, the operator using the measurement device 1 can execute a measurement operation with the measurement device 1 only after undergoing suitable testing or training. This maintains and improves the skill level of operators, and allows the implementation of specific testing and training by users to be managed more effectively.

The management device 2 according to an embodiment of the present application (an example of a management device) can be connected to a measurement device for measuring a specific substance contained in a sample, and comprises the second communication component 21 (an example of a second communication component or a communication component) configured to communicate with the measurement device1, the timer 24 (an example of a timer) configured to acquire clock time, the second memory 27 (an example of a second memory or a memory) capable of storing identification information for a plurality of users including first users, and the second controller 25 (an example of a second controller or a controller) configured to control the operation of the second communication component 21 and the timer 24. The second communication component 21 receives from the measurement device 1 first information that includes an evaluation result for the measurement operation acquired in a test mode executed by the measurement device 1, and identification information for a corresponding one of the first users. The second controller 25 executes a storage operation that associates the first information with first user identification information stored in the second memory 27 and stores the associated first information in the second memory 27 along with a first current time outputted from the timer 24. The second controller 25 also executes a determination operation that determines whether a second current time outputted from the timer 24 is within a specific length of time since the first current time of the newest first information, out of the first information for the corresponding one of the first users stored in the second memory 27. The second controller 25 also gives the measurement device 1 via the second communication component a command to execute a specific mode when having determined that the second current time is not within the specific length of time in the determination operation. At this point the specific mode is one that prohibits the execution of the measurement operation of the measurement device 1, and allows the measurement operation only when the test mode is executed.

With this configuration, the management device 2 can carry out processing to successively acquire and manage the implementation of specific testing and training by operators, and to limit the use of the measurement device 1 to operators. This reduces the burden on the administrator to manage the implementation of testing and training, reduces the risk that the administrator will overlook something, and allows the implementation of specific testing and training by users to be managed more effectively.

The measurement skill management system 100 pertaining to an embodiment of the present application comprises the measurement device 1 and the management device 2. The measurement skill management system 100 can maintain and improve the skill of operators, can reduce the risk that an administrator will overlook something, and allows the implementation of specific testing and training by users to be managed more effectively.

Other Embodiments

An embodiment was described above as an example of the technology disclosed herein. However, the technology disclosed herein is not limited to or by this embodiment, and can also be applied to embodiments to which suitable modifications, substitutions, additions, omissions, or the like have been made.

In view of this, other embodiments will be given below.

In the above embodiment, a blood glucose level measurement device was given as an example of the measurement device 1, but this is not the only option, and it may be any device for measuring specific information (such as cholesterol level, neutral fat level, albumin level, globulin level, oxygen saturation, hemoglobin level, myoglobin level, or uric acid value) by using a specific substance (such as blood, urine, tissue, or cells).

Also, in the above embodiment, the dedicated measurement device 1 for measuring a specific substance was given as an example, but this is not the only option. As disclosed in WO 2011/141908, for example, the measurement device 1 may make use of a smart phone or a tablet computer. In this case, for example, the detector 11 (detection device) is connected via USB (universal serial bus), headset jack, or the like to a smart phone or tablet computer in which a measurement device control program has been installed.

Some or all of the programs executed by the measurement device 1 or the management device 2 described in the above embodiment may be constituted by a single program.

In the measurement device and management device described in the above embodiment, the blocks may be individually made into chips by means of an integrated circuit or other such semiconductor device, or some or all of them may be combined into a single chip.

Some or all of the processing of the function blocks in the embodiment mentioned above may be realized by a computer program. Some or all of the processing of the function blocks in the embodiments mentioned above may thus be performed by the central processing unit (CPU) of a computer. Also, the programs for performing the various processing are stored on a hard disk, a ROM, or another such storage device, and are executed from the ROM or after being read to a RAM.

The processes in the above embodiment may be executed by hardware, or by software (including when execution by an OS (operating system), middle ware, or along with a specific library). Furthermore, a mixture of software and hardware may be employed.

The execution order of the processes in the processing method in the above embodiments is not limited to what was given in the above embodiment, and the order of execution can be switched around without departing from the gist of the invention.

The above embodiments are not limited to being in the form of a measurement device, a management device, or a measurement skill management system, and may instead be achieved by a measurement skill management method in which the measurement device or the management device is used, or by a computer program that executes the method.

Computer programs executed by a computer, and recording media to which these programs are recorded and which are capable of being read by a computer are encompassed by the scope of the present invention. Examples of recording media that can be read by a computer include flexible disks, hard disks, CD-ROM, MO, DVD, DVD-ROM, DVD-RAM, BD (Blu-ray Disc), and semiconductor memory.

The above-mentioned computer programs are not limited to being recorded to the above-mentioned recording media, and may instead be transmitted via an electrical communications circuit, a wired or wireless communications circuit, a network (typified by the Internet), or the like.

The measurement device pertaining to the present application is a blood glucose level measurement device or other such measurement device used in a hospital, for example, and is used as a measurement device for performing specific testing or training for an operator.

What is claimed:

1. A measurement device that measures a specific substance contained in a sample, the measurement device comprising:
   a detector configured to detect a signal based on the specific substance contained in the sample;
   a first manipulation component configured to allow plural kinds of input manipulation;
   a first controller configured to control an operation of the detector; and
   a first memory for storing identification information for a plurality of users,
   wherein the first controller is configured to:
      (i) receive first input information inputted via the first manipulation component,
      (ii) determine whether the first input information matches first identification information for a first user stored in the first memory,
      (iii) after determining that the first input information matches the first identification information, drive the detector in a state capable of detecting the signal based on the specific substance contained in the sample, put the measurement device in a state capable of performing a measurement operation that calculates a concentration of the specific substance contained in the sample on the basis of the detected signal, and then execute a specific mode that prohibits the first user from executing the measurement operation on the measurement device unless a test mode is executed,
      (iv) while the specific mode is being executed, receive second input information inputted via the first manipulation component by a second user, wherein the second user is different from the first user,
      (v) determine whether the second input information matches second identification information for the second user stored in the first memory, and
      (vi) after determining that the second input information matches the second identification information, halt the execution of the specific mode and execute the test mode to evaluate a measurement skill of the first user, wherein:
   in the test mode, the measurement operation is performed by using the detector and the first controller, and the measurement operation is evaluated by the second user.

2. The measurement device according to claim 1, wherein the first memory includes a first segment for storing the identification information for the first user, and a second segment for storing identification information for the second user.

* * * * *